(12) United States Patent
Beck et al.

(10) Patent No.: US 7,943,091 B2
(45) Date of Patent: May 17, 2011

(54) CHEMICAL EXPOSURE INDICATION DEVICE

(75) Inventors: Carl W. Beck, Haysville, KS (US); Rebecca L. Storey, Udall, KS (US)

(73) Assignee: The Boeing Company, Chicago, IL (US)

( * ) Notice: Subject to any disclaimer, the term of this patent is extended or adjusted under 35 U.S.C. 154(b) by 657 days.

(21) Appl. No.: 11/941,587

(22) Filed: Nov. 16, 2007

(65) Prior Publication Data

US 2009/0129984 A1    May 21, 2009

(51) Int. Cl.
*G01N 21/00* (2006.01)
*G01N 31/00* (2006.01)
*G01N 31/22* (2006.01)
*G01J 1/48* (2006.01)
G01N 33/52 (2006.01)
G01N 17/00 (2006.01)
B32B 9/00 (2006.01)

(52) U.S. Cl. ......... 422/82.05; 422/53; 422/87; 422/402; 116/206; 435/6; 435/902; 428/41.1; 428/654; 428/846.6; 428/846.7

(58) Field of Classification Search .................... 422/53; 116/206
See application file for complete search history.

(56) References Cited

U.S. PATENT DOCUMENTS

| 4,205,043 | A | | 5/1980 | Esch et al. |
| 5,192,500 | A | | 3/1993 | Treddenick |
| 5,198,335 | A | * | 3/1993 | Sekikawa et al. ................. 435/4 |
| 5,254,473 | A | * | 10/1993 | Patel ................................. 436/1 |
| 6,214,473 | B1 | * | 4/2001 | Hunt et al. ..................... 428/469 |
| 7,185,601 | B2 | * | 3/2007 | Carpenter et al. ............. 116/206 |
| 2003/0068824 | A1 | * | 4/2003 | Frankel et al. .................. 436/60 |
| 2004/0258561 | A1 | * | 12/2004 | Reimer et al. .................. 422/56 |
| 2006/0222564 | A1 | * | 10/2006 | Dale et al. ....................... 422/56 |
| 2008/0014117 | A1 | * | 1/2008 | Questel et al. .................. 422/56 |
| 2009/0023217 | A1 | * | 1/2009 | Lacy et al. ........................ 436/2 |

OTHER PUBLICATIONS

AWC II, Inc. Innovations of Acid/Base Detecting Products, downloaded from www.awc-2.com on Nov. 8, 2007; 5 pages.

* cited by examiner

*Primary Examiner* — Joseph W Drodge
*Assistant Examiner* — Jennifer Wecker
(74) *Attorney, Agent, or Firm* — McNees Wallace & Nurick LLC

(57) ABSTRACT

A chemical exposure indication device is disclosed. The device is removably attachable to a structure and includes a substrate having a first surface and a second surface and an indicating layer overlying the first substrate surface. The indicating layer includes a coating material that is chemically reactive with a pre-determined chemical compound that is known to degrade the structure. When the coating material is exposed to that corrosive compound in a pre-determined level associated with degradation of a metallic structure, the coating material provides a visual indication of the presence of the corrosive compound.

19 Claims, 3 Drawing Sheets

CHEMICAL EXPOSURE INDICATION DEVICE

STATEMENT OF FEDERALLY SPONSORED RESEARCH

This invention was made with Government support under contract number F29601-97-C-0001 by the United States Air Force. The Government has certain rights in this invention.

FIELD

The present invention relates to chemical detection and more particularly to devices for indicating chemical exposure.

BACKGROUND

In various industrial and military settings, the potential exists for exposure to corrosive or similarly hazardous chemicals. While analytical methods are available, they are unsatisfactory in many cases because they are expensive and time consuming and require trained personnel to operate and analyze the results. In many cases, other considerations mean that analytical methods are not an option even if cost were not an issue.

Prior non-analytical efforts to detect chemicals have been sought, but have focused primarily on the protection of humans using devices effective over a term typically measured in hours. Furthermore, levels of exposure that cause problems in materials are not necessarily the same as, and usually differ from, the types and levels of exposure that would pose danger to humans.

Non-analytical methods for protecting materials and equipment have largely been unsatisfactory, requiring significant amounts of time and expense associated with reactivation or stripping and re-coating after exposure. The processes of reactivation or stripping and recoating are hazardous, time consuming, expensive and may be incompatible with governmental environmental rules and regulations. Many coatings are also non-compatible with the structure to which they are applied, meaning that more expensive alternatives must be used, if available at all. Furthermore, in aircraft, the highest probability for chemical exposure of its exterior occurs when the aircraft is in flight, which is also the time when the exposure is most difficult to monitor through alternative techniques.

What is needed is a chemical indication exposure device that remains effective over long periods of time and which is capable of identifying harmful levels of chemical exposure for materials of construction, which often vary widely from harmful levels for humans.

SUMMARY

According to an exemplary embodiment of the invention, a chemical exposure indication device is disclosed. The device comprises a substrate having a first surface and a second surface, an indicating layer overlying the first substrate surface and means for removably attaching the device to a structure. The indicating layer comprises a coating material that is chemically reactive with a pre-determined chemical compound known to degrade the structure, such that when the coating material is exposed to a pre-determined level of the chemical compound, the coating material provides a visual indication of the compound's presence.

According to another exemplary embodiment of the invention, a chemical exposure indication device comprises a substrate having a first surface and a second surface, and means for attaching the substrate to a structure. The first substrate surface underlies an indicating layer of a coating material that is chemically reactive with a pre-determined corrosive chemical compound such that when exposed to a gaseous form of the chemical compound, the coating material changes color to provide a visual indication of the presence of the corrosive compound. The degree of color change is associated with the amount of corrosive compound to which the coating has been exposed. The device has an effective service period of at least one month in the absence of exposure to the pre-determined corrosive compound.

According to yet another embodiment, a chemical exposure indication device comprises a foil tape over-coated on one side with a layer of chemically reactive paint and having an adhesive on the other side. The paint changes color when the device is exposed to a pre-determined corrosive gas in a pre-determined amount that would cause degradation of a metallic structure to which the device is applied. The device has an effective service period of at least one month in the absence of exposure to the pre-determined corrosive gas.

One advantage of embodiments of the invention is that exposure to chemicals in amounts that cause degradation of metallic or polymeric structures can be detected.

Another advantage of an embodiment of the invention is that the exposure can be measured over long periods of time to measure cumulative exposure to corrosive chemicals.

Yet another advantage of embodiments of the invention is that when the device needs to be replaced, that can be accomplished quickly and easily without using environmentally unfriendly materials.

Still another advantage of an embodiment of the invention is that exposure to multiple different chemical compounds can be detected at the same time.

Other features and advantages of the present invention will be apparent from the following more detailed description of exemplary embodiments, taken in conjunction with the accompanying drawings which illustrate, by way of example, the principles of the invention.

BRIEF DESCRIPTION OF THE DRAWINGS

Where like parts appear in more than one drawing, it has been attempted to use like reference numerals for clarity.

DETAILED DESCRIPTION OF EXEMPLARY EMBODIMENTS

Exemplary embodiments of the invention are directed to chemical exposure indication devices that provide a visual indication when the device has been exposed to a pre-determined level of a corrosive chemical compound.

Figure 1:
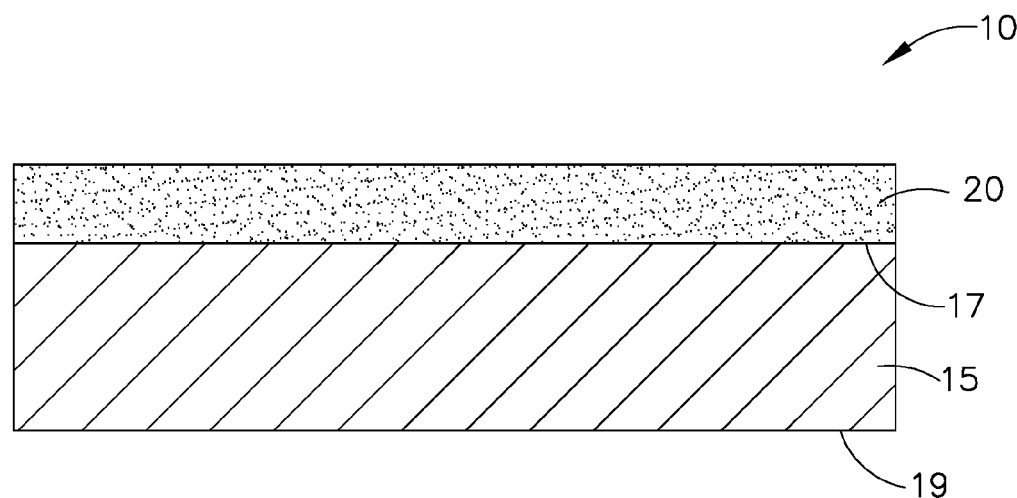
FIG. 1 illustrates a side view of a chemical exposure indication device in accordance with an embodiment of the invention.

Turning to FIG. 1, a side view of a chemical exposure indication device 10 is shown. The device 10 includes a substrate 15 having a first surface 17 and a second surface 19. An indicating layer 20 overlies the first surface 17 of the substrate 15.

The indicating layer 20 may be a coating of any material that chemically reacts when exposed to a pre-determined chemical compound to provide a visual indication that the exposure has occurred. In one embodiment, the indicating layer 20 changes from a first color to a second color in the presence of a pre-determined chemical compound. The coating is generally selected to be responsive to a particular chemical compound which degrades a metallic or polymeric structure, such that the color change occurs when the level of exposure reaches a pre-determined level that may be any level greater than zero. By "degrades" is meant that the chemical compound is corrosive to the structure or that the chemical compound accelerates environmentally assisted cracking of the structure, either of which can lead to premature failure of the structure.

Preferably, the pre-determined level of exposure is a level that is associated with degradation of a particular metallic structure of interest. In one embodiment, the color change occurs gradually, such that the cumulative effects of any level of exposure to the chemical compound of interest can qualitatively or quantitatively be assessed over time. As a result, if some exposure has occurred, it can quickly be determined whether the exposure levels warrant additional inspection.

The substrate 15 may be any metallic, ceramic, polymeric, natural or manufactured textile material or film that is compatible with the environment in which the device 10 will be used. The substrate 15 should also be compatible with the material(s) with which the substrate 15 will be coated. In one embodiment, the substrate 15 is aircraft speed tape or some other form of adhesive foil tape.

Chemical compounds which are particularly harmful to metallic or polymeric structures and which are of interest for detection include chlorine, iodine, ammonia, hydrogen peroxide, alcohols, such as methyl alcohol, and alkaline hydroxides (e.g., sodium hydroxide and potassium hydroxide). It will be appreciated that in most cases, the levels at which these compounds are harmful to structural materials are not the same as those in which the levels are harmful to humans. For example, humans are able to consistently be exposed to ammonia at levels of up to 1000 ppm, while as little as 5 to 20 ppm can have significant long term effects on metallic structures. As a result, the particular material for the indicating layer 20 is selected for both the chemical compound of interest and the level of exposure of interest for the particular structure. The material for the indicating layer 20 is also preferably responsive to the particular compound of interest in its gaseous and vapor (e.g. aerosol) forms.

In one embodiment, the indicating layer 20 is a color changing paint. Exemplary paints include paints that incorporate pH indicator or goldenrod dye. Another exemplary color changing paint is available under the trademark ON GUARD from AWC, II, Inc. of Smithville, Mo. After the color changing paint applied to the substrate 15 dries, the paint provides a dry chemistry for the indicating layer 20. This results in a device 10 that is effective for a month, six months, a year, or longer, unless spent earlier due to maximum exposure, at which point it would be replaced. That is, even after long service periods without exposure to the pre-determined compound with which the indicating layer 20 is associated, the device 10 will suffer no adverse effects and still function properly even if the first exposure to the particular compound does not occur until well after the device 10 is put in use. Sol-gels may also be used for the indicating layer 20, but due to their wet chemistry characteristics, an indicating layer 20 of a sol-gel material may become less effective more quickly and thus require more frequent replacement of the device 10.

Figure 2:
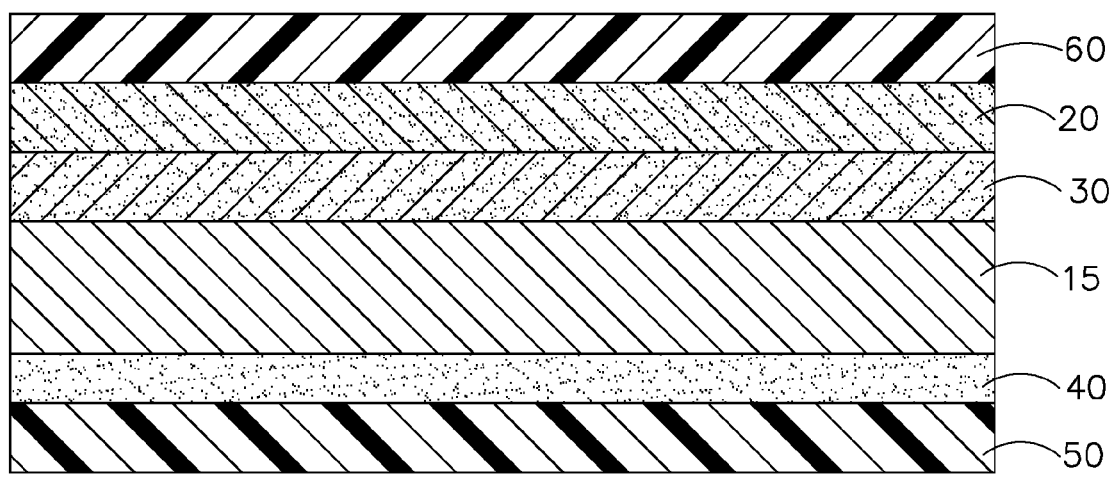
FIG. 2 illustrates a side view of a chemical exposure indication device in accordance with another embodiment of the invention.

The device 10 further includes a means for attaching the device 10 to a structure. The means for attaching the device 10 may be the substrate's second surface 19, or it may be a separate layer or device. For example, in one embodiment the substrate's second surface 19 may be magnetic, may have a static charge, or may be tacky, any of which could permit direct adherence of the second surface 19 to a structure. In another embodiment, as illustrated in FIG. 2, an additional adherent layer 40 may be added to impart the ability to attach the device 10 to a structure. The adherent layer 40 may be a separately applied layer of adhesive, double-stick tape, or a separate magnetic base, for example. Other suitable means for attaching the device 10 to a structure include mechanical fasteners, such as rivets, bolts, weldments, clamps, clips, a card frame or any combination of these.

As illustrated in FIG. 2, a removable backing layer 50 may be applied over the adherent layer 40 or directly to the substrate 15 to provide a "peel and stick" type device 10 which may be particularly useful where the device 10 is to be attached by an adhesive or through static cling. The backing layer 50 can be used to prevent premature adherence of the device 10 to something other than the desired location on the desired structure. As also illustrated in FIG. 2, a primer layer 30 may be used intermediate the substrate 15 and the indicating layer 20 to promote adhesion of the two layers. A removable protective layer 60 may also be provided over the indicating layer 20 so that the indicating layer 20 can be exposed to the environment at a desired point in time, such as after the device is attached to the desired structure.

Figure 3:
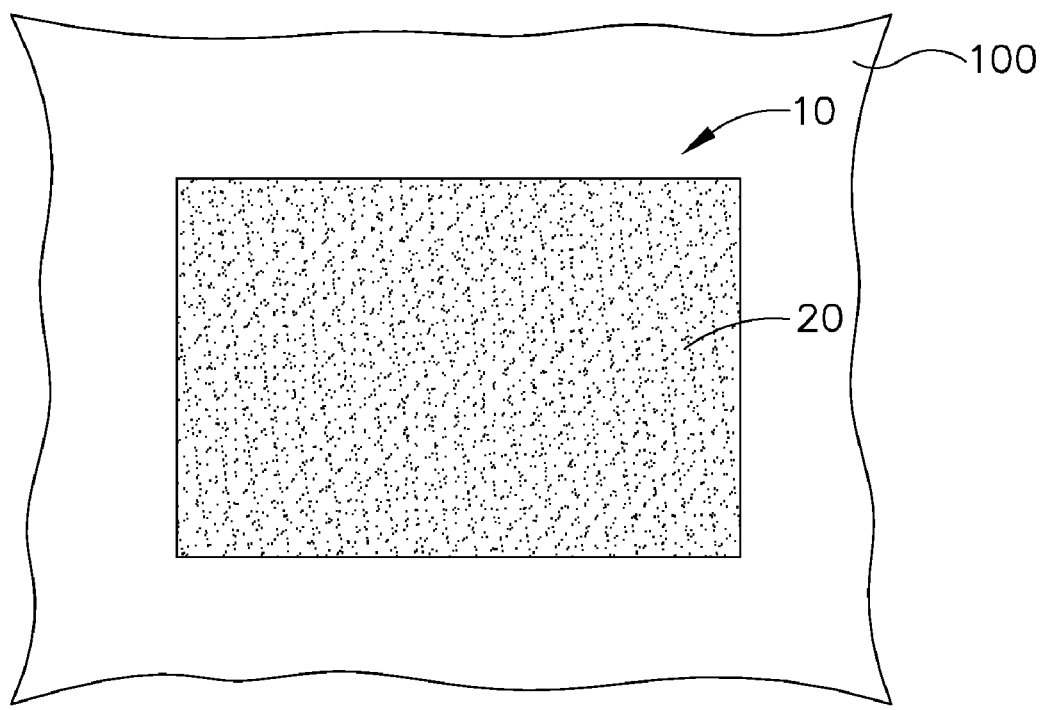
FIG. 3 illustrates a top view of a chemical exposure indication device in accordance with an embodiment of the invention.

Turning to FIG. 3, a top view of a chemical exposure indication device 10 is shown attached to a structure 100. Generally the structure 100 to which the device 10 is applied is at least partially constructed of the particular material for which exposure to one or more particular chemicals is desired to be monitored. However, the device 10 may be applied to a structure 100 that is in the same general location as the material to be monitored. In one embodiment, the structure 100 is an aircraft in which one or more devices 10 are placed at various locations on the exterior and interior of the aircraft. Particularly with respect to placement on exterior locations of an aircraft, the locations may be selected such that the devices 10 can be viewed using cameras so that in-flight monitoring of chemical exposure can be accomplished.

However, the structure 100 may be any structure that is constructed of, or is in the same environment as, a material for which exposure to particular chemical compounds is desired to be monitored. For example, the device may be used on a structure wherever it is desirable to detect chemical leakage, chemical jettison, chemical impingement, or chemical entrainment, by way of example only, that could damage the structure 100 or other equipment or materials in the vicinity of the structure 100 to which the device 10 is applied. Exemplary structures 100 include, without limitation, vehicles, aircraft, storage drums, and pipelines.

Figure 4:
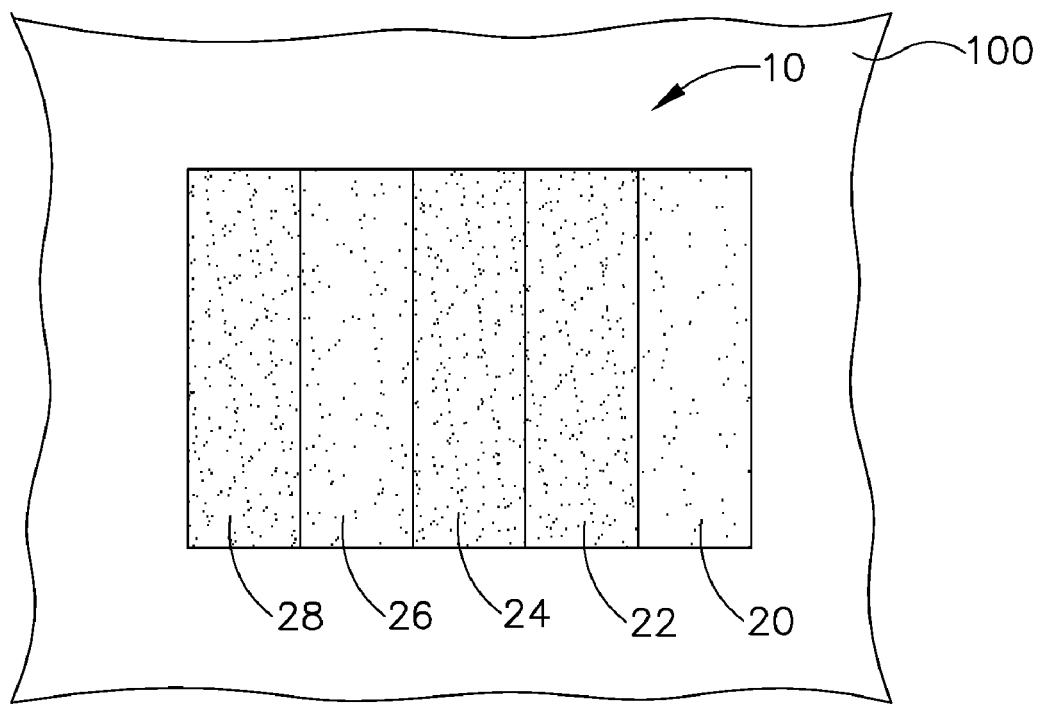
FIG. 4 illustrates a top view of a chemical exposure indication device in accordance with another embodiment of the invention.

As illustrated in FIG. 4, multiple different indicating layers 20, 22, 24, 26, 28 may be applied to the same substrate 15. Each indicating layer is associated with a different chemical compound, such that a single device 10 may be attached to a structure 100 for use in simultaneously detecting whether exposure has occurred to any one of several different chemical compounds.

Figure 5:
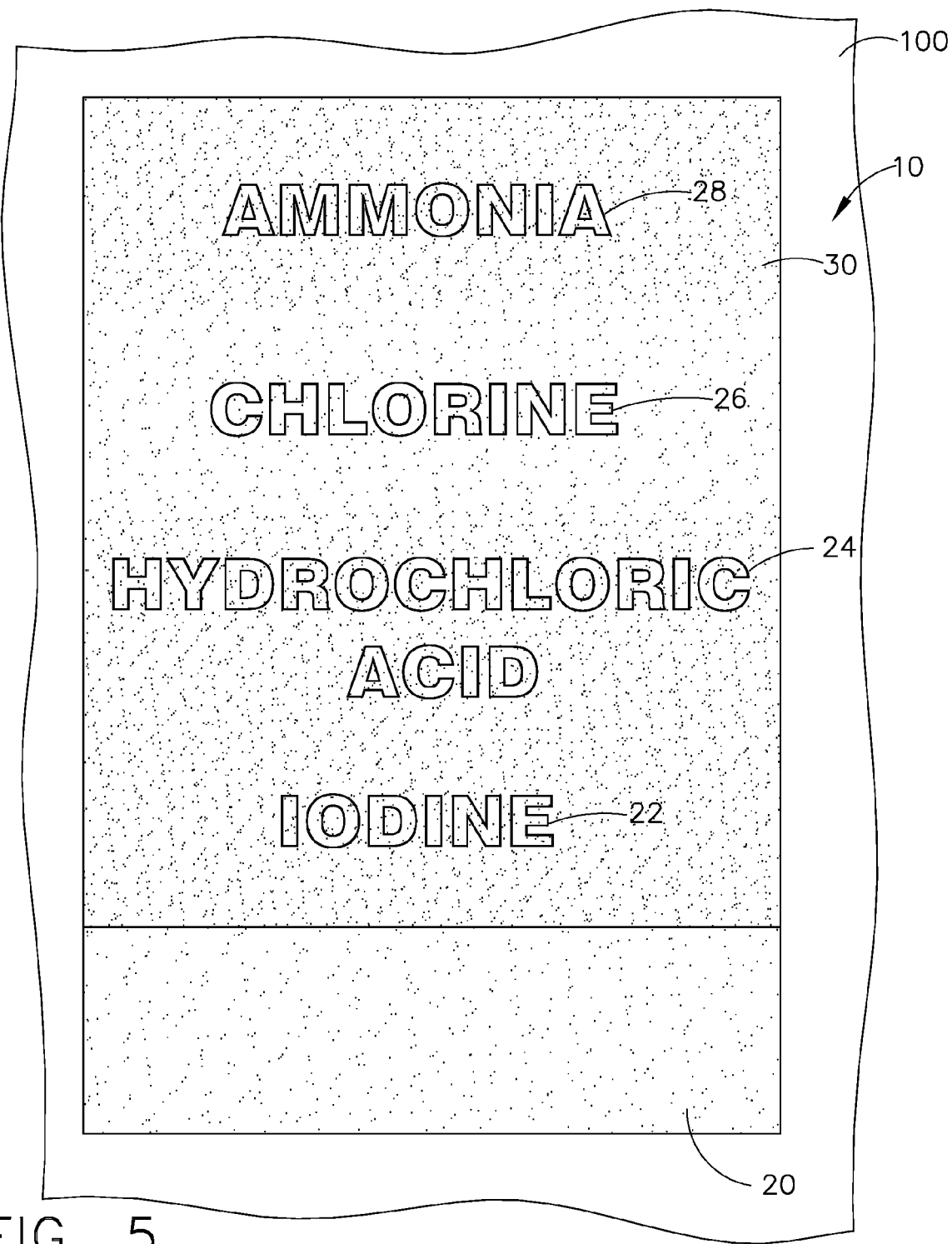
FIG. 5 illustrates a top view of a chemical exposure indication device in accordance with yet another embodiment of the invention.

FIG. 5 illustrates another embodiment in which one or more indicating layers 22 may be applied in the form of indicia, such that when the indicating layer 22 is exposed to the corresponding chemical compound, the indicia becomes apparent. As a result, when a particular indicating layer is exposed to its corresponding pre-determined chemical compound, only the letters or other form of indicia changes color. The indicia may be letters which spell out the name of the compound, a chemical formula, a chemical structure, or other any other pre-determined symbol that is selected to be associated with the particular chemical compound to which the indicating layer 22 corresponds.

To achieve the indicia, the indicating layer 22 is applied over only a portion of the substrate 15 or primer layer 30. The indicating layer 22 may be applied as the desired indicia, for example using a stencil, or alternatively, the indicating layer may be applied as the background (i.e. a reverse stencil), leaving the primer layer 30 or substrate 15 as the indicia. In either case, the indicating layer 22 results to form the indicia when the color change occurs. The substrate 15 or the primer layer 30 should be selected to match the pre-exposure color of the indicating layer. As a result, prior to exposure, the indicia cannot be seen, but when the indicating layer changes color, it is contrasted against the background of the primer layer 30 or substrate 15 that allows the indicia to easily be seen and easily identify the particular compound for which exposure has occurred.

Providing an indicating layer that results in the appearance of indicia upon exposure may be particularly useful when the exposure device 10 is used on the exterior of an aircraft or in other situations in which the device 10 is to be monitored via a closed-circuit camera. Closed circuit cameras are often black and white and vibration of a moving aircraft can make focusing on or resolving an overall color change challenging, but which is aided by the contrast of the indicia against the background. Applying the indicating layer 22 to form indicia may also avoid the need to identify or remember the order in which the indicating layers were applied before being able to subsequently determine to which chemical(s) the structure was exposed. The indicia is also useful in the event that the device 10 is inadvertently applied upside down, and thus may help to prevent misidentification of exposure to a particular chemical.

The means for attaching the device 10 to the substrate 100 is selected such that exemplary embodiments are readily removable from the structure 100 to which they are applied. That is, while the device 10 is adequately secured to the structure 100 so that it doesn't unintentionally come off even when attached to the exterior of an aircraft in flight, it can readily be removed for replacement after exposure or routine maintenance without the need to re-activate the indicating layer in place on the structure 100 and without wide-scale stripping and re-application. The device 10 can then be disposed of in an environmentally safe way. Alternatively, if re-activation is a possibility, it can be accomplished safely in a laboratory environment. Furthermore, potential damage to the structure 100 during stripping or re-activation operations is minimized.

While two or more indicating layers 20, 22 may be used on the same substrate 15, the use of multiple separate devices 10 each having a single indicating layer 20, each selected to indicate exposure to a different chemical compound, allows the devices 10 to be spaced apart from one another on the structure 100. This may decrease or avoid problems which can occur due to incompatibility between indicating layers 20 of different materials or other interference that can result in false indications. Additionally, because the indicating layer (s) 20 are applied to a substrate 15, and not directly to the structure 100, compatibility problems between the indicating layer 20 and the structure 100 are also avoided.

Exemplary embodiments provide a quick way to detect unsafe levels, or any levels depending on the material selected for a particular indicating layer, of a particular chemical compound without expensive, cumbersome and time consuming analytical testing devices and equipment and can therefore be accomplished by untrained personnel. Thus, embodiments of the current invention may find use in military applications, as well as in commodity and specialty chemical industries, the pulp and paper industry, mining and refining industries, petroleum and petrochemical industries, fuel handling and delivery industries, transportation industries, food packaging and processing, refrigeration manufacturing, packaging, installation and monitoring and municipal applications, by way of example only.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A chemical exposure indication device comprising:
a substrate having a first surface and a second surface;
an indicating layer overlying the first substrate surface; and
means for removably attaching the device to a metallic structure,
wherein the indicating layer comprises a coating material that is chemically reactive with a pre-determined chemical compound known to degrade the structure, such that when the coating material is exposed to a pre-determined level of the chemical compound, the coating material provides a visual indication of the compound's presence;
wherein the pre-determined level of exposure corresponds to a level of exposure to the compound that is associated with degradation of the metallic structure;
and wherein the coating material is chemically reactive with a chemical compound selected from the group consisting of ammonia, chlorine, hydrogen peroxide, iodine, alkaline hydroxides, and alcohols.

2. The device of claim 1, wherein the means for attaching is selected from the group consisting of an adhesive, a magnetic base, a magnetic polymer, static cling, mechanical fasteners, and double stick tape.

3. The device of claim 1, wherein the coating material is color changing paint.

4. The device of claim 1, wherein the coating material is a sol-gel.

5. The device of claim 1, wherein the device has an effective service period of greater than one month in the absence of exposure to the pre-determined chemical compound.

6. The device of claim 1, wherein the coating material is chemically reactive with a chemical compound selected from the group consisting of ammonia, chlorine, hydrogen peroxide, iodine, alkaline hydroxides, and alcohols.

7. The device of claim 1, wherein the device is attached to an exterior surface of an aircraft.

8. The device of claim 1, wherein the indicating layer is in contact with the first surface of the substrate.

9. The device of claim 1, wherein a primer layer is intermediate the first surface of the substrate and the indicating layer.

10. The device of claim 1, comprising a plurality of indicating layers separately overlying the first surface of the substrate.

11. The device of claim 1, wherein the indicating layer is to form indicia, such that the indicia becomes visible with the indicating layer is exposed to the pre-determined level of the chemical compound.

12. The device of claim 1, further comprising a removable protective layer overlying the indicating layer.

13. The device of claim 1, wherein the substrate is constructed of a material selected from the group consisting of metallic, ceramic, polymeric, natural textile, and manufactured textile.

14. The device of claim 1, wherein the substrate is adhesive foil tape.

15. The device of claim 1, wherein the means for attachment is an adherent layer in contact with the second surface of the substrate.

16. The device of claim 1, wherein the means for attachment is the second surface of the substrate.

17. The device of claim 1, further comprising a removable backing layer underlying the substrate.

18. A chemical exposure indication device comprising:
a substrate having a first surface and a second surface, the first surface underlying an indicating layer of a coating material that is chemically reactive with a pre-determined corrosive chemical compound, such that when exposed to a gaseous form of the chemical compound, the coating material changes color to provide a visual indication of the presence of the corrosive compound; and means for attaching the substrate to the metallic structure;

and wherein the coating material is chemically reactive with a chemical compound selected from the group consisting of ammonia, chlorine, hydrogen peroxide, iodine, alkaline hydroxides, and alcohols, wherein the degree of color change is associated with the amount of corrosive compound to which the coating has been exposed and wherein the device has an effective service period of at least one month in the absence of exposure to the pre-determined corrosive compound.

19. A chemical exposure indication device comprising:
a foil tape over-coated on one side with a layer of chemically reactive paint, which is reactive with a chemical compound selected from the group consisting of ammonia, chlorine, hydrogen peroxide, iodine, alkaline hydroxides, and alcohols, and having an adhesive on the other side, wherein the paint changes color when the device is exposed to a pre-determined corrosive gas in a pre-determined amount that would cause degradation of a metallic structure to which the device is applied, and wherein the device has an effective service period of at least one month in the absence of exposure to the pre-determined corrosive gas.

* * * * *